United States Patent [19]

Biftu et al.

[11] Patent Number: 4,536,512
[45] Date of Patent: Aug. 20, 1985

[54] 5-(2,3-DIHYDRO-1H-PYRROLIZIN-5-OYL)-2,3-DIHYDRO-1H-PYRROLIZINE-1-ALKANOIC OR CARBOXYLIC ACIDS AND USE THEREOF AS ANTI-INFLAMMATORY AND ANALGESIC AGENTS

[75] Inventors: Tesfaye Biftu; Bruce E. Witzel; Peter L. Barker, all of Westfield, N.J.

[73] Assignee: Merck & Co., Inc., Rahway, N.J.

[21] Appl. No.: 433,339

[22] Filed: Oct. 8, 1982

[51] Int. Cl.$^3$ .................. A61K 31/40; C07D 487/06
[52] U.S. Cl. ..................................... 514/413; 548/453
[58] Field of Search ......................... 548/453; 424/274

[56] References Cited

U.S. PATENT DOCUMENTS

| | | | |
|---|---|---|---|
| 3,952,012 | 4/1976 | Carson | 424/274 |
| 4,048,191 | 9/1977 | Carson | 424/274 |
| 4,087,539 | 5/1978 | Muchowski | 424/274 |
| 4,097,579 | 6/1978 | Muchowski | 424/274 |
| 4,119,639 | 10/1978 | Carson | 424/274 |
| 4,232,038 | 11/1980 | Muchowski | 424/274 |

OTHER PUBLICATIONS

Carson and Wong, *J. Med. Chem.*, 16, (2), 172, (1973).

*Primary Examiner*—Glennon H. Hollrah
*Assistant Examiner*—D. B. Springer
*Attorney, Agent, or Firm*—Theresa Y. Cheng; Mario A. Monaco

[57] ABSTRACT

New 5-(2,3-dihydro-1H-pyrrolizin-5-oyl)-, 5-(2,3-dihydro-1H-pyrrolo[2,1-b]thiazol-5-oyl)-, 5-(2,3-dihydro-1H-pyrrolo[2,1-b]imidazol-5-oyl)-, and 5-(2,3-dihydro-1H-pyrrolo[2,1-b]oxazol-5-oyl)-derivatives of substituted 2,3-dihydro-1H-pyrrolizine-1-alkanoic or carboxylic acids have been prepared. They are found to be effective inhibitors of platelet aggregation and are analgesic/anti-inflammatory agents with low ulcerogenic side effects.

7 Claims, No Drawings

5-(2,3-DIHYDRO-1H-PYRROLIZIN-5-OYL)-2,3-DIHYDRO-1H-PYRROLIZINE-1-ALKANOIC OR CARBOXYLIC ACIDS AND USE THEREOF AS ANTI-INFLAMMATORY AND ANALGESIC AGENTS

BACKGROUND OF THE INVENTION

The present invention relates to novel 5-(2,3-dihydro-1H-pyrrolizin-5-oyl)-, 5-(2,3-dihydro-1H-pyrrolo[2,1-b]thiazol-5-oyl)-, 5-(2,3-dihydro-1H-pyrrolo[2,1-b]imidazol-5-oyl)-, and 5-(2,3-dihydro-1H-pyrrolo[2,1-b]oxazol-5-oyl)- derivatives of substituted 2,3-dihydro-1H-pyrrolizine-1-alkanoic or carboxylic acids and their corresponding salts, esters, nitriles, amides and substituted amides. These compounds are found to exhibit analgesic/anti-inflammatory activities with low ulcerogenic irritation and are effective inhibitors of platelet aggregation. For a chronic disease, for example, arthritis, it is crucial that the anti-inflammatory/analgesic agent be administered routinely and regularly at an effective dosage level without causing gastric irritation or ulcers.

Accordingly, it is an object of the present invention
(1) to provide novel nonsteroidal antiinflammatory and analgesic agents of lower ulcerogenic side effect;
(2) to develop processes for the preparation of the novel compounds;
(3) to provide methods of application of the novel compounds in the treatment of inflammatory diseases; and
(4) to provide pharmaceutical compositions and formulations for the administration of these novel compounds.

DETAILED DESCRIPTION OF THE INVENTION

This invention relates to novel 5-(2,3-dihydro-1H-pyrrolizin-5-oyl)-2,3-dihydro-1H-pyrrolizine-1-alkanoic or carboxylic acids and analogs of the structural formula:

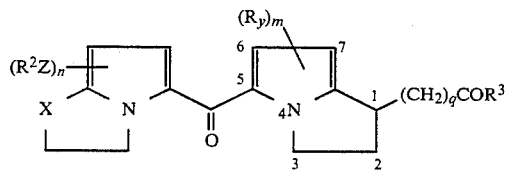

or a pharmaceutically acceptable salt, ester or amide thereof wherein
R is
(a) hydrogen;
(b) loweralkyl especially $C_{1-6}$ linear or branched alkyl such as methyl, ethyl, propyl, isopropyl, t-butyl, pentyl, and hexyl;
(c) lowercycloalkyl especially $C_{3-6}$ cycloalkyl such as cyclopropyl, cyclobutyl, cyclopentyl and cyclohexyl;
(d) lower(cycloalkylalkyl) especially $C_{4-8}$ (cycloalkylalkyl) such as cyclopropylmethyl, cyclopentylmethyl, cyclohexylmethyl and cyclohexylethyl;
(e) loweralkenyl especially $C_{2-8}$ alkenyl such as 2-propenyl, 2-methyl-2-butenyl and 3-ethyl-2-pentenyl;
(f) haloloweralkyl especially halo $C_{1-6}$ alkyl such as chloromethyl, trifluoromethyl, 1-chloroethyl and 2,2-difluorobutyl;
(g) phenyl- or substituted phenyl-loweralkyl especially phenyl-$C_{1-3}$ alkyl such as benzyl, 4-chlorobenzyl, 2-fluorobenzyl, and phenylpropyl; or
(h) phenyl or substituted phenyl such as p-methoxyphenyl, m-chlorophenyl.

groups (a)–(h) above being unsubstituted or substituted by loweralkyl, loweralkoxy, halo, cyano, carboxy, sulfamoyl, carbamoyl, sulfonyl, sulfinyl, azido, amino, substituted amino such as loweralkylamino or di(loweralkyl)amino, haloalkyl, carboxyalkyl, carbamoylalkyl, N-substituted carbamoylalkyl or a combination thereof;

m is 0 to 2;
q is 0 to 6;
$R^2Z$ can be at any available ring positions and Rhu 2 is R as previously defined;
n is 0 to 2;
$R^3$ is
(a) hydroxy;
(b) loweralkoxy especially $C_{1-6}$ alkoxy such as methoxy, ethoxy, isopropoxy or n-butoxy;
(c) amino;
(d) loweralkylamino especially $C_{1-6}$ alkylamino such as cyclohexylamino, methylamino, isopropyl amino, n-butylamino or t-butylamino;
(e) diloweralkylamino especially di($C_{1-6}$ alkyl)amino such as diethylamino, dimethylamino, or ethylmethylamino;
(f) morpholinyl;
(g) bis(hydroxyloweralkyl)amino especially bis(hydroxy $C_{1-6}$ alkyl)amino such as bis(hydroxyethyl)amino;
(h) loweralkycyclohexylamino especially $C_{1-6}$ alkylcyclohexyamino such as methylcyclohexylamino;
(i) glucosamino;
(j) lower(alkanoyloxyalkoxy), especially $C_{1-6}$ (alkanoyloxyalkoxy) such as 2-(pivaloyloxy)ethoxy or 2-(acetoxy)ethoxy;
(k) aroyloxyloweralkoxy especially 1-(benzyloxy)ethoxy;
(l) lower(alkoxycarbonyloxyalkoxy) especially $C_{1-6}$ (alkoxycarbonyloxyalkoxy) or hydroxycarbonylalkoxy such as 2-(ethoxycarbonyloxy)ethoxy or $HOOCCH_2O-$;
(m) hydroxyalkyloxycarbonyloxyalkoxy or polyhydroxyalkyloxycarbonyloxyalkoxy for example,

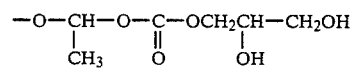

and

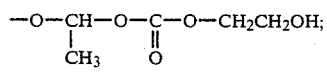

(n) aryloxycarbonyloxyloweralkoxy especially aryloxycarbonyl $C_{1-6}$ alkoxy such as 2-(phenoxycarbonyloxy)ethoxy;
(o) di(loweralkyl)amino loweralkoxy especially di $C_{1-6}$alkyl)amino $C_{1-6}$ alkoxy such as 2-dimethylamino-ethoxy, 2-dimethylamino-n-propoxy, or 3-diethylamino-n-butoxy;

(p) lower(alkanoylaminoalkoxy), especially $C_{1-6}$ (alkanoylaminoalkoxy) such as acetamidoethoxy;
(q) imidoloweralkoxy especially imido $C_{1-6}$ alkoxy such as 2-(1-succinimido)ethoxy;
(r) heterocyclyloxy, or heterocycloalkylalkoxy, for example, phthalidyloxy, 2-pyridyloxy,

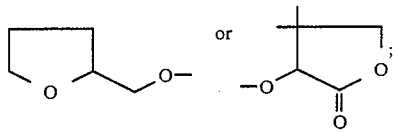

(s) hydroxyloweralkoxy especially hydroxy $C_{1-6}$ alkoxy such as hydroxypropoxy;
(t) loweralkoxyalkoxy especially $C_{1-6}$ (alkoxyalkoxy) such as methoxyethoxy, ethoxyethoxy or methoxymethoxy;
(u) lower dialkylaminoalkylamino such as $(C_2H_5)_2NCH_2CH_2NH-$;
(v) N-pyrrolidinylloweralkoxy especially N-pyrrolidinyl $C_{1-6}$ alkoxy such as N-pyrrolidinylethoxy or N-pyrrolidinyl methoxy and N-methyl-2-pyrrolidinylmethoxy;
(w) N-piperidinylloweralkoxy especially N-piperidinyl $C_{1-6}$ alkoxy such as N-piperidinylethoxy;
(x) N-morpholinylloweralkoxy especially N-morpholinyl $C_{1-6}$alkoxy such as N-morpholinylethoxy; or
(y) 4-methyl-1-piperazinylloweralkoxy especially 4-methyl-1-piperazinyl $C_{1-6}$ alkoxy such as 4-methyl-1-piperazinylethoxy;

X is $-O-$, $-S-$, $-SO-$, $-SO_2-$, $-NR^4-$ or $-CHR^4-$;
Y is $-O-$, $-S-$, $-SO-$, $-SO_2-$, $CHR^4-$ or hydrogen providing that when Y is hydrogen, R does not exist;
Z is $-O-$, $-S-$, $-SO-$, $-SO_2-$, $-NR^4-$, $-CHR^4$ or halo especially fluoro, chloro or bromo providing that when Z is halo, $R^2$ does not exist; and
$R^4$ is hydrogen or $C_{1-6}$ alkyl as previously defined.

The preferred embodiment of this invention comprises compounds of formula (I) wherein R is
(a) hydrogen or $C_{1-6}$ alkyl as previously defined;
(b) $C_{2-4}$ alkenyl such as 2-propenyl or propenylmethyl;
(c) halo$C_{1-6}$ alkyl as previously defined; or
(d) phenyl-$C_{1-3}$ alkyl such as benzyl;
m is 0 or 1;
$R^2Z$ is as defined above;
q is 0 to 2;
n is 0 or 1;
$R^3$ is hydroxy, $C_{1-6}$ alkoxy, or lower(alkanoylaminoalkoxy), especially $C_{1-6}$ alkanoylaminoalkoxy such as acetamidoethoxy;
X is $-S-$, $-SO-$ or $-CHR^4-$;
$R^4$ is hydrogen or methyl;
Y is $-O-$, $-S-$, $-CH_2-$, or H when R is absent; and
Z is $-S-$, $-CH_2-$, or halo when $R^2$ is absent.

The most preferred embodiment of this invention comprises compounds of structural formula (I) wherein:
R is absent or $C_{1-3}$ alkyl especially methyl;
m is 0 or 1;
q is 0 or 1;
$R^2Z$ is as defined previously;
n is 0 or 1;
$R^3$ is hydroxy, $C_{1-6}$ alkoxy or acetamidoethoxy;
X is $-S-$, $-SO-$, or $-CHR^4-$;
Y is oxygen, $CH_2-$, or H with the proviso that when Y is H, R is absent;
Z is $-S-$, $-CH_2-$, or halo with the proviso that when Z is halo, $R^2$ is absent; and
$R^4$ is hydrogen or methyl.

Representative compounds of this invention are as follows:
(a) 5-(2,3-Dihydro-1H-pyrrolizin-5-oyl)-6-methyl-2,3-dihydro-1H-pyrrolizine-1-carboxylic acid.
(b) 5-(2,3-dihydropyrrolo[2,1-b]thiazol-5-oyl)-6-methyl-2,3-dihydro-1H-pyrrolizine-1-carboxylic acid.
(c) Ethyl 5-(2,3-dihydro-1H-pyrrolo[2,1-b]imidazol-5-oyl)-6-methyl-2,3-dihydro-1H-pyrrolizine-1-carboxylate.
(d) Ethyl 5(2,3-dihydro-1-methyl-1H-pyrrolizin-5-oyl)-6-methyl-2,3-dihydro-1H-pyrrolizine-1-carboxylate.
(e) Ethyl 5-(2,3-dihydropyrrolo[2,1-b]thiazol-5-oyl)-6-methyl-2,3-dihydro-1H-pyrrolizine-1-carboxylate-S-oxide.
(f) Ethyl 5-(2,3-dihydro-1H-pyrrolizone-5-oyl)-6-methyl-2,3-dihydro-1H-pyrrolizine-1-acetate.
(g) 5-(2,3-Dihydro-1-methyl-1H-pyrrolizin-5-oyl)-6-methyl-2,3-dihydro-1H-pyrrolizine-1-carboxylic acid.

The novel compounds of the present invention can be prepared from the precursor IIa as shown in the following scheme:

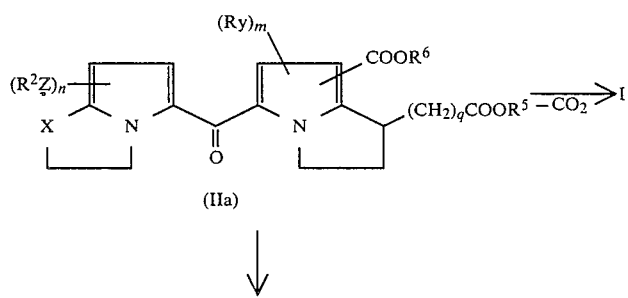

(IIa)

-continued

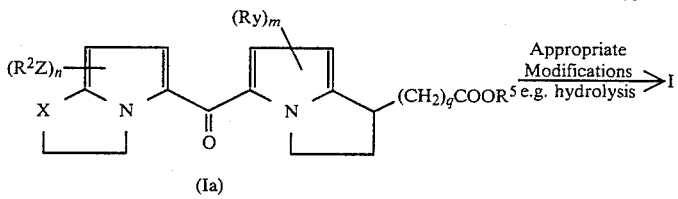

wherein n, m, q, R, R², X, Y and Z are as previously defined and $R^5$ is hydrogen, loweralkyl especially $C_{1-6}$ alkyl such as methyl, ethyl, isopropyl, t-butyl, n-butyl, pentyl, or cyclohexyl, and $R^6$ is hydrogen, t-butyl, benzhydryl or other protecting groups which can be removed under mild conditions. IIa can be directly decarboxylated to I when $R^5$ and $R^6$ are independently hydrogen, t-butyl- or benzhydryl.

According to the scheme above, IIa is decarboxylated under neutral, acidic or basic conditions or by itself (neat). When the decarboxylation is conducted under basic conditions, the precursor of formula IIa is usually heated with a base (Table I) in an appropriate solvent at about 50°–250° C. preferably about 90°–150° C. for about 0.5–48 hours or until the decarboxylation is substantially complete.

The most commonly utilized solvents comprise
(1) water;
(2) $C_{1-20}$ alkanol especially methanol, ethanol, isopropanol and t-butyl alcohol;
(3) lower ketone, e.g., acetone and methylethylketone;
(4) lower ether including diethylether, 1,2-dimethoxyethane, tetrahydrofuran (THF), dioxane and diglyme;
(5) a mixture of at least two of the solvents described in (1) to (4).

TABLE I

Organic Bases Used in Decarboxylation

Tri-(loweralkyl)amine, e.g., triethylamine
pyrrolidine
pyridine
collidine
ethanolamine
quinoline, etc.

When acidic decarboxylation is applied, IIa is refluxed in trifluoroacetic acid, for example, to give Ia which is then subject to various known modifications such as hydrolysis (when $R^4$ is not H), aminolysis, ester exchange etc. to afford (I). Other acids may also be used. For example, those listed below in Table II.

TABLE II

Acids Used in the Decarboxylation (1) An acid of the structural formula:

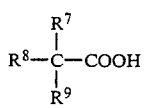

wherein $R^7$ and $R^9$ independently are hydrogen or halo such as iodo, bromo, chloro or fluoro preferably chloro or fluoro; and $R^8$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.

(2) Preferred Acids:
Acetic acid
Chloroacetic acid
Chlorodifluoroacetic acid
Dichloroacetic acid
Difluoroacetic acid
Trifluoroacetic acid
Trichloroacetic acid
Pentafluoropropanoic acid.

The acidic decarboxylation may be conducted in an acid or in an inert solvent containing the acid. The solvents which are often used are illustrated below in Table III.

TABLE III

Solvents for the Acidic Decarboxylation

Toluene
Benzene
Xylene
Tetrahydrofuran
1,2-Dimethoxyethane
Dioxane
Methylene chloride
Acetic Acid The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 75° C.

Generally, the decarboxylation is substantially complete after heating at an appropriate temperature for about 1 to about 20 hours or under more favorable conditions, about 0.5 hours to about 5 hours.

The novel compounds of the present invention can also be obtained from precursor Ia via hydrolysis following the same procedures described in copending application Ser. No. 373,692 filed May 3, 1982. These procedures are incorporated herein by reference.

The precursors having formula Ia or IIa are readily prepared from condensation between a 2,3-dihydro-1H-pyrrolizine-1-alkanoic acid moiety (IIIa) and a substituted 2,3-dihydro-1H-pyrrolizine or analogs as shown below in scheme (a):

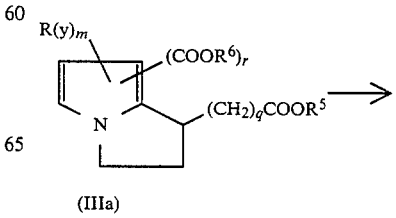

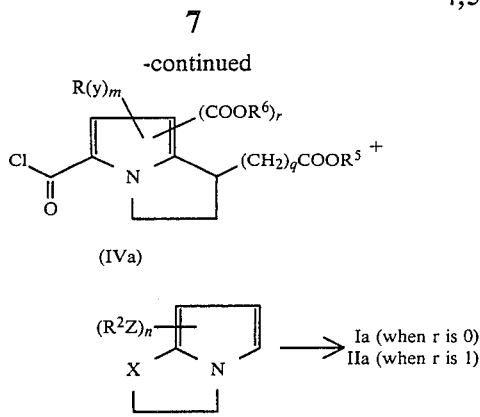

wherein R, $R^2$, $R^5$, $R^6$, m, n, q, X, Y and Z are as previously defined; and r is 0 or 1.

Alternatively, Ia or IIa may be obtained via the following route (b):

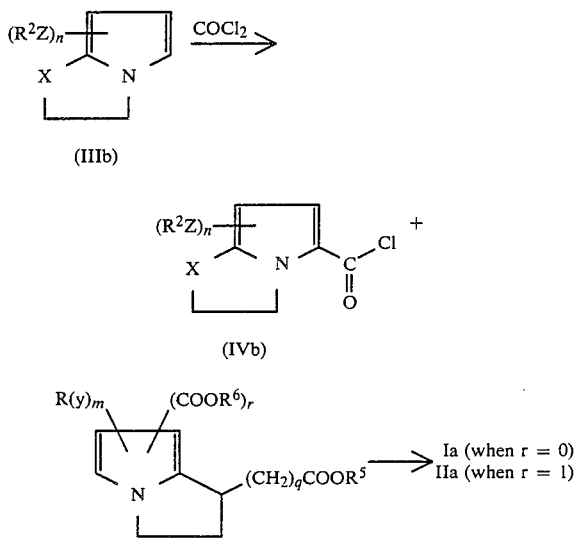

The starting materials of formula

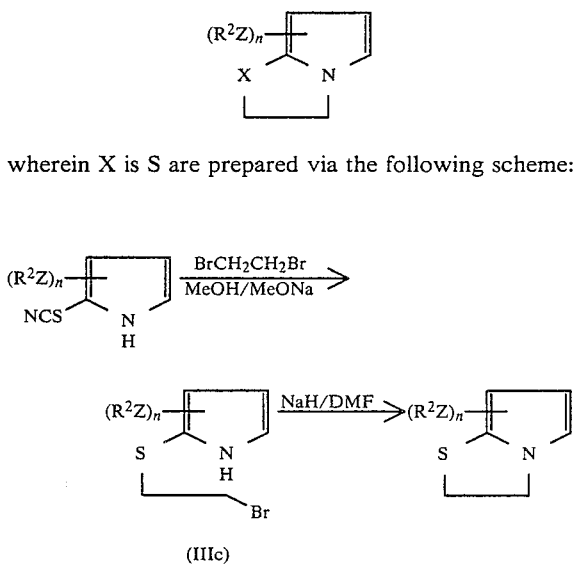

wherein X is S are prepared via the following scheme:

A substituted or unsubstituted 2-thiocyanopyrrole is first treated with $XCH_2CH_2X$ (where X represents halo eg., bromo, chloro or iodo) preferably $BrCH_2CH_2Br$, in the presence of a base and an organic solvent such as lower alkanol including ethanol, isopropanol, n-butanol; dioxane, tetrahydrofuran, 1,2-dimethoxyethane, diglyme or the like. The preferred bases are sodium salts of lower alkanols especially sodium methoxide, sodium ethoxide or sodium t-butoxide. However, other strong bases such as sodium hydroxide, potassium hydroxide, or triton B may also be used. This reaction is usually carried out under mild conditions, i.e., at about $-78°$ C. to about the reflux temperature of the solvent. Preferably the reaction is run at from about $-10°$ C. to about 35° C. until completion, yielding the intermediate 2-haloethylthiopyrrole derivative, IIIc.

Subsequently, ring closure of IIIc to derivatives of 2,3-dihydropyrrolo[2,1-b]thiazole is accomplished by treatment of IIIc with a base preferably sodium hydride in an aprotic solvent, e.g., N,N-dimethylformamide (DMF), dimethylsulfoxide (DMSO) or the like. The ring closure is usually carried out at room temperatures or lower although mild heating may be applied when necessary.

Alternatively, 2,3-dihydropyrrolo[2,1-b]thiazole and its derivatives may be prepared by reacting a 2-thiocyanopyrrole with a haloacetic acid, e.g., chloro or bromoacetic acid in the presence of a base to form a 2-(-2-pyrrolothio)acetic acid. The acetic acid function is then converted to the desired 2-halo ethyl derivative of formula IIIc.

Other routes to 2,3-dihydropyrrolo[2,1-b]thiazole via pyrrole, 2-aminopyrrole, N-(2-haloethyl) pyrrole and other similar compounds may also be used. These routes require no further description as they are obvious to those skilled in the art.

Starting materials other than those described above are known or readily preparable by procedures described in copending application Ser. No. 387,079, filed June 9, 1982 and U.S. Pat. No. 4,097,579. These two disclosures are herein incorporated by reference.

The pharmaceutically acceptable salts of the acids of the Formula I are readily prepared by conventional procedures well-known in the art. For example, an acid of Formula I is treated with an appropriate amount of a base, such as an alkali or alkaline earth metal hydroxide, e.g. sodium hydroxide, potassium hydroxide, calcium hydroxide, or an organic base such as an amine, e.g., triethylamine, lysine, dibenzylethylenediamine, piperidine, pyrrolidine, benzylamine and the like.

The pharmaceutically acceptable esters of the acids of structural formula (I) are prepared by conventional methods. For example, (1) A compound of Formula (I) is treated with a lower alkanol or phenol in the presence of an acid such as sulfuric acid, hydrochloric acid, boron trifluoride or the like.

(2) A compound of Formula (I) is converted to an acid halide such as acid chloride or bromide via treatment with a halogenating agent such as thionyl chloride or phosphorus pentachloride, followed by reaction with an alcohol or a phenol.

(3) A compound of Formula (I) is treated with an alcohol in the presence of a condensing agent such as N,N'-dicyclohexyl-carbodiimide or the like.

Other well-known methods such as those included in the "Compendium of Organic Synthetic Methods," I.

T. Harrison et al., Wiley-Interscience, p. 272 (1971), may also be used.

Similarly, the pharmaceutically acceptable amides of the acids of Formula (I) are readily prepared by conventional methods. For example, the halides of the acids of Formula (I) can be treated with ammonia or substituted amines such as ethylamine, benzylamine or glucosamine to afford the corresponding amides. Other methods involving treatment of the acids with an amine in the presence of a catalyst such as DCC or other similar condensing agents may also be used.

The novel compounds of this invention are anti-inflammatory and analgesic agents of value in the treatment of a wide variety of conditions where one or more of the symptoms of pain or inflammation are manifested, e.g., rheumatoid arthritis, osteoarthritis, gout, infectious arthritis, rheumatic fever and pain symptoms associated with other diseases.

For treatment of inflammation, fever or pain, the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active compounds of formula (I) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be, for example inert diluents, such as calcium carbonate, sodium carbonate, lactose, calcium phosphate or sodium phosphate; granulating and disintegrating agents, for example maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl- or n-propyl-p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day ). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are provided for illustrating but not limiting the scope of the present invention.

EXAMPLE 1

Ethyl 5-(2,3-dihydro-1H-pyrrolizin-5-oyl)-6-methyl-2,3-dihydro-1H-pyrrolizine-1-carboxylate Step A: Preparation of 2,3-dihydro-1H-pyrrolizine-5-carbonyl chloride To a stirred, ice-bath cooled portion (30 ml) of 12.5% phosgene in toluene was added a solution of 2,3-dihydro-1H-pyrrolizine (0.80 g, 0.0074 m) in ether (30 ml) dropwise over ca two minutes. After stirring cold for ca 2.5 hr, the reaction mixture is allowed to warm to room temperature, the volatiles are removed in vacuo, and the resultant crystalline 2,3-dihydro-1H-pyrrolizine-5-carbonyl chloride used as is in the next step.

Step B: Preparation of diethyl 5-(2,3-dihydro-1H-pyrrolizin-5-oyl)-6-methyl-2,3-dihydro-1H-pyrrolizine-1,7-dicarboxylate To an ice-bath cooled solution of diethyl 6-methyl-2,3-dihydro-1H-pyrrolizine-1,7-dicarboxylate (2.0 g, 0.0075 m) in methylene chloride (25 ml) was added stannic chloride (2.6 ml, 0.0225 m) all at once. A solution of 2,3-dihydro-1H-pyrrolizine-5-carbonyl chloride (1.1 g, 0.0075 m) in methylene chloride (10 ml) was then added dropwise, and the resultant mixture stirred cold for two hours, then at ambient temperatures overnight. The reaction mixture was then quenched with excess ice-$H_2O$ and ether, the organic layer removed, washed well with water, dried over sodium sulfate, filtered, and concentrated in vacuo to a residue. Trituration with either yielded 1.75 g of diethyl 5-(2,3-dihydro-1H-pyrrolizin-5-oyl)-6-methyl-2,3-dihydro-1H-pyrrolizine-1,7-dicarboxylate as a white solid.

Step C: Preparation of 5-(2,3-dihydro-1H-pyrrolizin-5-oyl)-6-methyl-2,3-dihydro-1H-pyrrolizine-1,7-dicarboxylic acid A mixture of the diester from Step B (1.62 g, 0.004 m), methanol (15 ml), water (5 ml), and potassium hydroxide (1.6 g, 0.026 m) was refluxed in an inert atmosphere for 5.5 hours, cooled, diluted with water (ca. 80 ml), filtered, the filtrate acidified with 2N hydrochloric acid, and the cooled, aged mixture filtered. After drying the well-washed (water) solid, 1.4 g of 5-(2,3-dihydro-1H-pyrrolizin-5-oyl)-6-methyl-2,3-dihydro-1H-pyrrolizine-1,7-dicarboxylic acid is obtained as a white solid.

Step D: Preparation of ethyl 5-(2,3-dihydro-1H-pyrrolizin-5-oyl)-7-carboxy-6-methyl-2,3-dihydro-1H-pyrrolizine-1-carboxylate A stirred mixture of the diacid from Step C above (1.3 g, 0.0038 m), ethanol (30 ml) and resin catalyst (1.3 g; Biorad AG 50W-XB) was heated under reflux for 10 hours in an inert atmosphere, filtered hot, the solution allowed to cool, ice-bath cooled and filtered to yield ethyl 5-(2,3-dihydro-1H-pyrrolizine- 5-oyl)-7-carboxy-6-methyl-2,3-dihydro-1H-pyrrolizine-1-carboxylate (0.73 g) as a white solid.

Alternatively, the esterification may be run in alcohol at room temperature using a small amount of mineral acid (e.g. sulfuric acid) as catalyst.

Step E: Preparation of Ethyl 5-(2,3-dihydro-1H-pyrrolizin-5-oyl)-6-methyl-2,3-dihydro-1H-pyrrolizine-1-carboxylate A stirred portion (0.63 g, 0.0007 m) of the acid from Step D above in an oxygen-free atmosphere is set in an oil-bath set at 210° C. (and rising to 230° C.) and kept there until carbon dioxide evolution ceases. Chromatography of the residue obtained, using a silica gel column and 25% ethyl acetate/hexane as eluant yields pure ethyl 5-(2,3-dihydro-1H-pyrrolizin-5-oyl)-6-methyl-2,3-dihydro-1H-pyrrolizine-1-carboxylate.

The decarboxylation may be carried out by other means well known to those in the art, e.g., by heating of its copper salt in quinoline, heating in ethanolamine, treatment with trifluoroacetic acid, etc.

Saponification of this ester in the usual manner yields the corresponding acid, 5-(2,3-dihydro-1H-pyrrolizin-5-oyl)-6-methyl-2,3-dihydro-1H-pyrrolizine-1-carboxylic acid, m.p. 167–170° C.

EXAMPLE 2

Ethyl 5-(2,3-dihydropyrrolo(2,1-b)thiazol-5-oyl)-6-methyl-2,3-dihydro-1H-pyrrolizine-1-carboxylate Step A: Preparation of 2,3-dihydropyrrolo(2,1-b) thiazole A stirred mixture of 2-thiocyano-pyrrole (8.7 g, 0.07 m; *J. Org. Chem.*, 22 (1957) 1500), 1,2-dibromoethane (155 ml) and methanol (140 ml) was ice-bath cooled in an oxygen-free atmosphere, and sodium methoxide (9.5 g, 0.17 m) added. The resultant highly-colored mixture was allowed to stir cold and then at ambient temperature overnight. The resultant mixture was distributed between ether and water (500 ml), the ether extracts washed, dried and concentrated to a residue which on chromatography on silica gel using a hexane and then 20% ethylacetate/hexane system as eluant yielded 2(2-bromoethylthio)pyrrole (4.6 g). This was dissolved in dry N,N-dimethylformamide (80 ml), covered with an oxygen-free atmosphere, ice-bath cooled, and reacted with sodium hydride (1.2 g of 60% dispersion in mineral oil). After stirring overnight at ambient temperatures the reaction mixture was partitioned between ether and water, the ether layer washed with water until the dimethylformamide was removed, dried and concentrated to 2,3-dihydropyrrolo(2,1-b)thiazole.

Step B: Preparation of ethyl 5-(2,3-dihydropyrrolo[2,1-b]thiazol-5-oyl)-6-methyl-2,3-dihydro-1H-pyrrolizine-1-carboxylate When 2,3-dihydropyrrolo[2,1-b]thiazole was used in place of 2,3-dihydro-1H-pyrrolizine in the procedures of Examples 1, Step A through Step E, there was obtained the ethyl 5-(2,3-dihydropyrrolo [2,1-b]thiazol-5-oyl)-6-methyl-2,3-dihydro-1H-pyrrolizine-1-carboxylate and corresponding acid, i.e., 5-(2,3-dihydropyrrolo(2,1-b)thiazol-5-oyl-methyl-2,3-dihydro-1H-pyrrolizine-1-carboxylic acid, m.p. 177°–178° C. The ethyl ester has a melting point of 146°–148° C.

Following substantially the same procedures as described above, the following compounds were also prepared from their corresponding starting materials:

| Starting Materials | Compound |
| --- | --- |
| 2,3-dihydropyrrolo[2,1-b]oxazole | ethyl 5-(2,3-dihydropyrrolo[2,1-b]oxazol-5-oyl)-6-methyl-2,3-dihydro-1H—pyrrolizine-1-carboxylate and the corresponding acid. |
| 2,3-dihydropyrrolo[2,1-b]imidazole | ethyl 5-(2,3-dihydropyrrolo[2,1-b]-imidazol-5-oyl)-6-methyl-2,3-dihydro-1H—pyrrolizine-1-carboxylate and the corresponding acid. |

EXAMPLE 3

Ethyl 5-(2,3-dihydro-1-methyl-1H-pyrrolizin-5-oyl)-6-methyl-2,3-dihydro-1H-pyrrolizine-1-carboxylate Step A: Preparation of 2,3-dihydro-1-methyl-1H-pyrrolizine A solution of 2,3-dihydro-1-oxo-1H-pyrrolizine (16.1 g, 0.133 m); *J. Org. Chem.*, 27 2468 (1962) ) in dried dimethylsulfoxide (60 ml) is added dropwise over ca. 10 minutes to a mixture of methylenetriphenylphosphorane (from methyl triphenylphosphonium bromide (57.2 g, 0.16 m), sodium hydride 60% dispersion (6.4 g, 0.16 m) and dimethylsulfoxide (256 ml) in the standard fashion (*J. Org. Chem.*, 28 1128 (1963)) at ambient temperatures. After stirring for ca 2 hours, the mixture is heated in an oil-bath set at 70° C. for ca 30 minutes, and let cool. After stirring overnight at ambient temperatures, the mixture is poured into 1200 ml of ice-water, extracted 4×400 ml of ether, the ether layers washed 3×400 ml of water, dried and concentrated to a residue. The residue is extracted well with hexane, the filtered hexane extracts concentrated and distilled to yield 2,3-dihydro-1-methylene-1H-pyrrolizine.

Reduction of this material in methanol using a 5% palladium on carbon catalyst in a 40 p.s.i. hydrogen atmosphere yields 2,3-dihydro-1-methyl-1H-pyrrolizine.

Step B: Preparation of ethyl 5-(2,3-dihydro-1-methyl-1H-pyrrolizin-5-oyl)-6-methyl-2,3-dihydro-1H-pyrrolizine-1-carboxylate When 2,3-dihydro-1-methyl-1H-pyrrolizine is used in place of 2,3-dihydro-1H-pyrrolizine in Example 1, Step A to Step E, there is obtained ethyl 5-(2,3-dihydro-1-methyl-1H-pyrrolizin-5-oyl)-6 -methyl-2,3-dihydro-1H-pyrrolizine-1-carboxylate.

Hydrolysis of this ester in the usual manner yields 5-(2,3-dihydro-1-methyl-1H-pyrrolizin-oyl)-6-methyl-2,3-dihydro-1H-pyrrolizine-1-carboxylic acid.

EXAMPLE 4

Ethyl 5-(2,3-dihydro-1H pyrrolizin-5-oyl)-2,3-dihydro-1H-pyrrolizine-1-acetate

Step A: Preparation of ethyl 2,3-dihydro-1H-pyrrolizine-1-acetate

When carboethoxymethylene triphenylphosphonium bromide is used in place of methyl triphenylphosphonium bromide in Example 3, Step A, and the complete reaction sequence described therein is carried out there is obtained ethyl 2,3-dihydro-1H-pyrrolizine-1-acetate.

Step B: Preparation of Ethyl 5-(2,3-dihydro-1H-pyrrolizin-5-oyl)-2,3-dihydro-1H-pyrrolizine-1-acetate When ethyl 2,3-dihydro-1H-pyrrolizine-1-acetate is reacted with phosgene as described in Example 1, Step A, and the resulting ethyl 5-(chlorocarbonyl)-2,3-dihydro-1H-pyrrolizine-1-acetate reacted with 2,3-dihydro-1H-pyrrolizine as described in Example 2, ethyl-5-2,3-dihydro-1H-pyrrolizin-5-oyl)-2,3-dihydro-1H-pyrrolizine-1-acetate is obtained.

Hydrolysis of the acetate in the normal manner yields the corresponding acid, i.e., 5-(2,3-dihydro-1H-pyrrolizin-5-oyl)-2,3-dihydro-1H-pyrrolizine-1-acetic acid.

What is claimed is:

1. A compound of formula

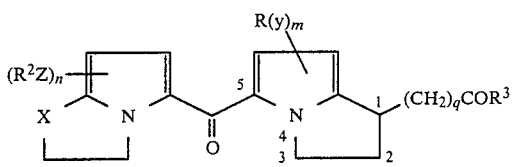

or a pharmaceutically acceptable salt thereof wherein:
R is
(a) H or $C_{1-6}$ alkyl;
(b) $C_{2-4}$ alkenyl;
(c) halo-$C_{1-6}$ alkyl; or
(d) phenyl-$C_{1-3}$ alkyl;
m is 0 or 1;
$R^2Z$ can be at any available position and $R^2$ is R;
q is 0 to 2;
n is 0 to 1;
$R^3$ is hydroxy, $C_{1-6}$ alkoxy or $C_{1-6}$ (alkanoylaminoalkoxy);
X is —$CHR^4$—;
Y is —O—, —S—, $CH_2$— or H with the proviso that when Y is H, R is absent; and
Z is —S—, —$CH_2$— or halo with the proviso that when Z is halo, $R^2$ is absent, $R^4$ is hydrogen or $C_{1-6}$ alkyl.

2. The compound of claim 1 wherein
R is absent or $C_{1-3}$ alkyl;
m is 0 or 1;
q is 0;
n is 0 or 1;
$R^3$ is hydroxy, $C_{1-6}$ alkoxy or acetamidoethoxy;
X is $CHR^4$—;
Y is —O—, $CH_2$— or H with the proviso that when Y is H, R is absent;
Z is —S—, —$CH_2$—, or halo with the proviso that when Z is halo, $R^2$ is absent; and
$R^4$ is hydrogen or methyl.

3. The compound of claim 1 which is:
(a) 5-(2,3-Dihdryo-1H-pyrrolizin-5-oyl)-6-methyl-2,3-dihydro-1H-pyrrolizine -1-carboxylic acid;
(b) Ethyl 5-(2,3-dihydro-1-methyl-1H-pyrrolizin-5-oyl)-6-methyl-2,3-dihydro-1H-pyrrolizine-1-carboxylate;
(c) Ethyl 5-(2,3-dihydro-1H-pyrrolizine-5-oyl)-6-methyl-2,3-dihydro-1H-pyrrolizine-1-acetate;
(d) 5-(2,3-dihydro-1-methyl-1H-pyrrolizin-5-oyl)-methyl-2,3-dihydro-1H-pyrrolizine-1-carboxylic acid.

4. A pharmaceutical composition for treating inflammatory conditions, fever and pain in mammalian species comprising a non-toxic pharmaceutical carrier and an effective amount of a compound of formula

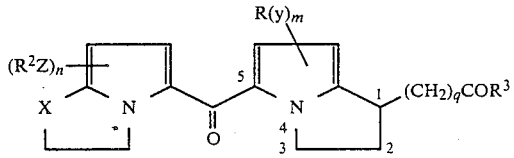

or a pharmaceutically acceptable salt thereof wherein:
R is
(a) H or $C_{1-6}$ alkyl;
(b) $C_{2-4}$ alkenyl;
(c) halo-$C_{1-6}$ alkyl; or
(d) phenyl-$C_{1-3}$ alkyl;
m is 0 or 1;
$R^2Z$ can be at any available position and $R^2$ is R;
q is 0 to 2;
n is 0 to 1;
$R^3$ is hydroxy, $C_{1-6}$ alkoxy or $C_{1-6}$ (alkanoylaminoalkoxy);
X is —$CHR^4$—;
Y is —O—, —S—, $CH_2$— or H with the proviso that when Y is H, R is absent; and
Z is —S—, —$CH_2$— or halo with the proviso that when Z is halo, $R^2$ is absent, $R^4$ is hydrogen or $C_{1-6}$ alkyl.

5. The pharmaceutical composition of claim 4 wherein
R is absent or $C_{1-3}$ alkyl;
m is 0 or 1;
q is 0;
n is 0 or 1;
$R^3$ is hydroxy, $C_{1-6}$ alkoxy or acetamidoethoxy;
X is $CHR^4$—;
Y is —O—, $CH_2$— or H with the proviso that when Y is H, R is absent;
Z is —S—, —$CH_2$—, or halo with the proviso that when Z is halo, $R^2$ is absent; and
$R^4$ is hydrogen or methyl.

6. A method of treatment of inflammatory conditions, fever and pain which comprises the administration to a mammmalian species in need of such treatment an effective amount of a compound of formula

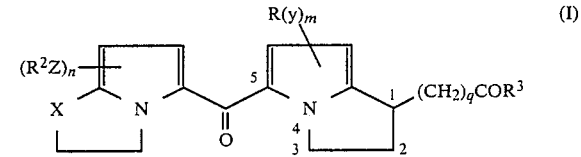

or a pharmaceutically acceptable salt thereof wherein:
R is
(a) H or $C_{1-6}$ alkyl;
(b) $C_{2-4}$ alkenyl;
(c) halo-$C_{1-6}$ alkyl; or
(d) phenyl-$C_{1-3}$ alkyl;
m is 0 or 1;
$R^2Z$ can be at any available position and $R^2$ is R;
q is 0 to 2;
n is 0 to 1;
$R^3$ is hydroxy, $C_{1-6}$ alkoxy or $C_{1-6}$ (alkanoylaminoalkoxy);
X is —$CHR^4$—;
Y is —O—, —S—, $CH_2$— or H with the proviso that when Y is H, R is absent; and
Z is —S—, —$CH_2$— or halo with the proviso that when Z is halo, $R^2$ is absent, $R^4$ is hydrogen or $C_{1-6}$ alkyl.

7. The method of claim 6 wherein
R is absent or $C_{1-3}$ alkyl;
m is 0 or 1;
q is 0;
n is 0 or 1;
$R^3$ is hydroxy, $C_{1-6}$ alkoxy or acetamidoethoxy;
X is $CHR^4$—;
Y is —O—, $CH_2$— or H with the proviso that when Y is H, R is absent;
Z is —S—, —$CH_2 13$ , or halo with the proviso that when Z is halo, $R^2$ is absent; and
$R^4$ is hydrogen or methyl.

* * * * *